(12) United States Patent
Ongaro

(10) Patent No.: US 6,926,874 B2
(45) Date of Patent: Aug. 9, 2005

(54) AUTOCLAVE

(75) Inventor: Daniele Giovanni Ongaro, Villa di Serio (IT)

(73) Assignee: W & H Sterilization srl, Seriate (IT)

( * ) Notice: Subject to any disclaimer, the term of this patent is extended or adjusted under 35 U.S.C. 154(b) by 558 days.

(21) Appl. No.: 10/170,175

(22) Filed: Jun. 12, 2002

(65) Prior Publication Data

US 2003/0007915 A1 Jan. 9, 2003

(30) Foreign Application Priority Data

Jul. 3, 2001 (AT) ...................................... A 1031/2001

(51) Int. Cl.[7] .............................................. A61L 2/06
(52) U.S. Cl. ......................... 422/298; 122/441; 95/257
(58) Field of Search ........................ 422/298; 210/126; 95/241, 257; 122/441

(56) References Cited

U.S. PATENT DOCUMENTS

| | | | | |
|---|---|---|---|---|
| 4,465,027 A | * | 8/1984 | Steinegger | 122/406.4 |
| 4,583,301 A | * | 4/1986 | Crowley et al. | 34/73 |
| 5,480,610 A | * | 1/1996 | Birkholz et al. | 422/26 |

* cited by examiner

Primary Examiner—John Kim
Assistant Examiner—Sean Conley
(74) Attorney, Agent, or Firm—Friedrich Kueffner

(57) ABSTRACT

The invention relates to an autoclave for sterilising medical and in particular dental appliances and instruments, with a chamber (13), in which the appliances to be sterilised are located, with a steam generator (5), connected with the chamber (13) and a condensate pipe (34) connecting the chamber (13) with a condenser (19), and a further pipe (39) connecting the condenser (19) with a vacuum pump (20) and finally leading into a tank.

The invention is characterised in that the condensate (water-steam mixture) in the pipe (39) is passed into a separator vessel (40), that a connecting pipe (41) extends from the upper area of said separator vessel (40), preferably from its highest point, to the vacuum pump (20), that said separator vessel (40) is provided in its lower area, preferably at its lowest point, with a one-way valve (45) which in the presence of an appropriate pressure difference permits discharge of fluid from the separator vessel (40) into a collector vessel (43), that a pressure pipe (42) coming from the vacuum pump (20) ends in the upper area of said collector vessel (43) and that a transfer pipe (44) leads into the main tank (38) of the autoclave from the lower area of said collector vessel (43).

2 Claims, 4 Drawing Sheets

FIG. 3
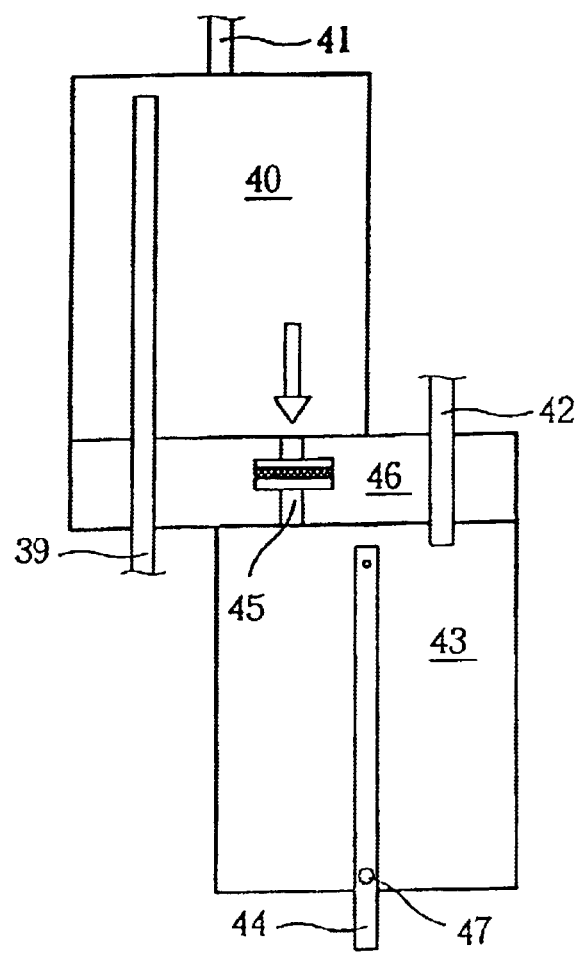
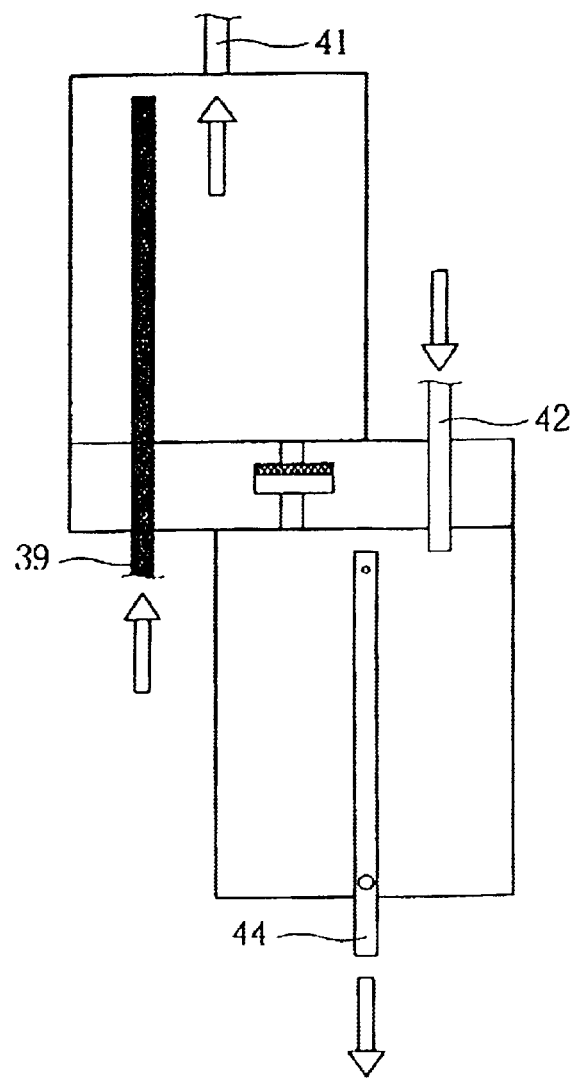
FIG. 4

FIG. 5
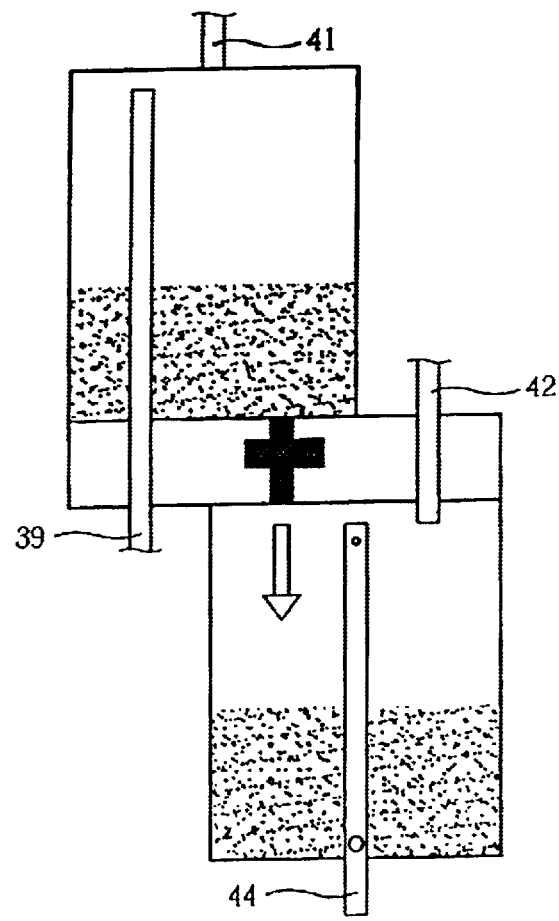
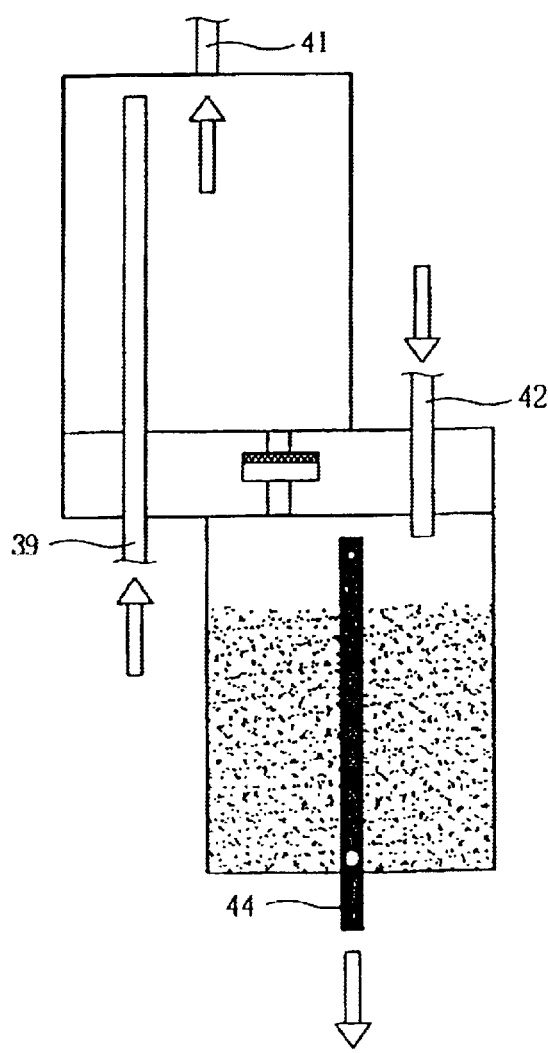
FIG. 6

US 6,926,874 B2

1

AUTOCLAVE

The invention relates to an autoclave for sterilising medical and in particular dental appliances and instruments. Such an autoclave is known e.g. from EP 0 992 247 A1.

The design of such autoclaves should be rather compact and their consumption of properly purified and thus expensive water required for the generation of steam as low as possible and permit a high throughput rate and in particular avoid long heating periods. As reliability and mechanical robustness of such apparatus are an indispensable prerequisite, it is a constant goal to improve the individual component parts of such autoclaves in this respect and to try to use less and less space so as to provide a larger and more conveniently accessible autoclave chamber proper in which the instruments and appliances to be sterilised are placed, resulting in the same performance and without any additional space required.

During the operation of such autoclaves the pressure and the temperature in the chamber are increased, maintained, lowered and raised again in the different cycles according to the different regulations in order to reliably destroy all germs and to remove any impurities or germs present in the apparatus due to the circulation of steam and condensate which is the unavoidable consequence of cyclic heating and cooling and to eliminate these from the autoclave chamber.

Ultimate condensation of the steam takes place in a condenser which is usually air cooled in order to render the apparatus independent of water. A vacuum pump for emptying the autoclave chamber and transporting the condensate to an intermediate tank is provided—seen from the steam side—behind the condenser and a sound absorber. The magnetic valves used are costly and need maintenance in addition to space, which, as outlined above, is a disadvantage.

The aim of the invention is to provide a simplified and cheap solution requiring less space. According to the invention these aims are achieved in that, coming from the condenser, the condensate (water-steam mixture) is passed into a separator vessel, that a connecting pipe extends from the upper area of said separator vessel, preferably from its highest point, to the vacuum pump, that said separator vessel is provided in its lower area, preferably at its lowest point, with a one-way valve which may be spring-loaded which in the presence of an appropriate pressure difference permits discharge of fluid from the separator vessel into a collector vessel, that a pressure pipe coming from the vacuum pump ends in the upper area of said collector vessel and that the pipe leads into the main tank of the autoclave from the lower area of said collector vessel.

In this way the condensate collects in the separator chamber when the condenser and the vacuum pump are operated, the one-way valve is kept closed by the vacuum applied in this chamber and by connecting the outlet of the vacuum pump to the collector vessel; when the condensation cycle is finished, the pressure in the separator vessel and the collector vessel is equalised by switching off the vacuum pump so that due to the weight of the separated liquid pressing on it the liquid runs off from the separator vessel into the collector vessel; when the condensation cycle starts anew, the liquid contained in the collector is passed through the connecting pipe to the main tank by connecting the outlet of the vacuum pump to the collector vessel, while at the same time, in most cases somewhat deferred, condensate is passed anew into the separator vessel through the pipe coming from the condenser.

In this way the costly electromagnetic valves used so far become superfluous, the various connecting pipes may com-

2 pletely be dispensed with; preferably the separator vessel and the collector vessel have identical design and the shape of a pot, and are mounted in a somewhat staggered arrangement on a mounting plate so that the one-way valve connecting the two vessels may be positioned directly in the mounting plate. The other pipes may be appropriately mounted in the mounting plate or in the bottom area of the collector vessel which corresponds to the top area of the separator vessel when mounted upside down.

The invention is disclosed in greater detail by means of the drawing.

FIGS. 3 to 6 show the separator and collector vessels according to the invention in different operating stages.

FIG. 1 shows a diagrammatic view of the autoclave known from the prior art to which the invention may be applied. It has the following features:

Figure 1:
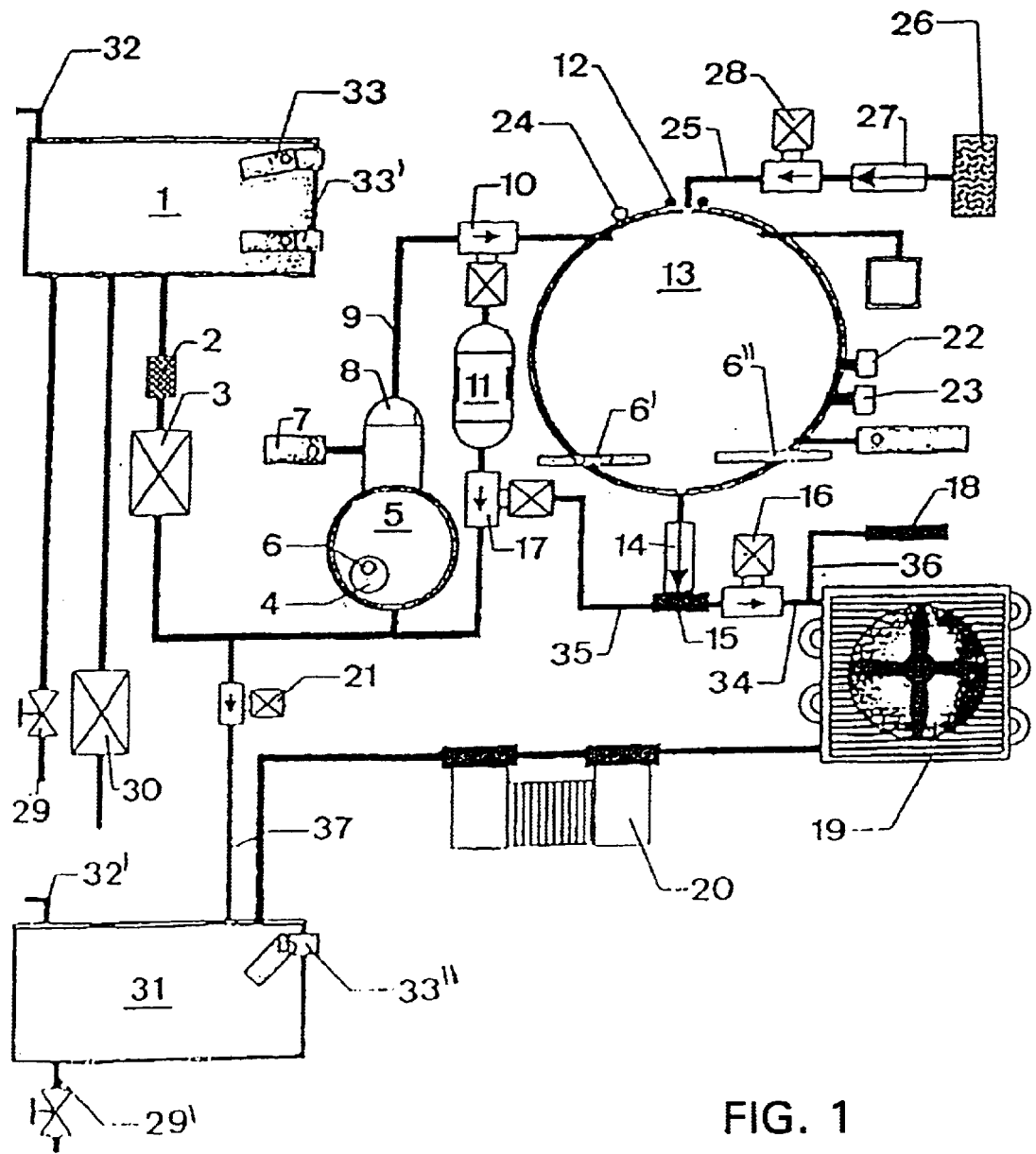
FIG. 1 shows an autoclave according to the prior art.

The process water, taken from a tank 1 through a filter 2, is injected by a pump 3 in a steam generator 5. The steam generator 5 is equipped with an eccentric positioned heating element 4 and a temperature sensor 6.

A safety valve 7 is connected to the steam generator. A tube 9 links the steam dome 8 of the generator 5 to a three way valve 10 and depending on it's position, to the chamber 13 or the condensation accumulator 11.

When the three way valve 10 is switched, the steam reaches the chamber 13 and the pressure in the chamber increases. When the chamber 13 is drained, the steam streams through a one way valve 14, an embranchement 15, through a tube 34 and a drain valve 16 to a condenser 19 and is pumped off by the vacuum pump 20 into a waste tank 31.

During the pressure pulses and the sterilisation process, the drain valve 16 is kept closed and the chamber is connected to the condensation collector 11 through branching 15 to a tube 35 to another three way valve 17, its position in these phases depending on the position of the above mentioned three way valve 10. The condensation collector 11 is directly linked to the chamber but it's temperature is lower. This "cold point" creates a physical phenomenon similar to a little vacuum, sucking out the condensation from the chamber 13. From here it is discharged in regular intervals into the steam generator 5 to be heated up again. This process according to the invention saves water, energy and time.

An air-inlet-valve 18 is connected to the pipe 34 downstream of the valve 15 but upstream of the condenser 19. Through this valve 18 and its pipe 36, a precisely predetermined quantity of air is added to the condenser-bound steam for two reasons: Firstly to obtain a perfect and continuous drain of the condenser and secondly to allow the membrane pump 20 to suck directly water thereby guaranteeing a low noise level.

Of course these so called "vacuum losses" are therefore determined in relation to the flow rate of the membrane pump 20 in a way to reach easily the predetermined optimal values in all the vacuum phases.

In the meantime, during the vacuum phases, it is possible to heat up the steam generator 5 in order to "accumulate" steam for the next pressure pulse. As soon as the pressure in the chamber 13 has dropped to the predetermined value, the drain valve 16 is closed and both three way valves 10 and 17 are so switched that the steam prepared in the steam generator 5 is injected into the chamber 13 and the condensation which has been formed in chamber 13 is extracted and returned through the condensation collector 11 to the steam generator 5, until predetermined pressure and temperature values are reached again in chamber 13.

Having reached this stage, new vacuum/pressure pulses can start, and so on.

With the successive vacuum and pressure phases it is possible to reach a residual air percentage of less than 0,1%. In a preferred embodiment, in order to reduce and optimise the duration of the air expulse procedure and the total cycle, a time out has been fixed for the first three vacuum pulses (ex: 3 min). If the vacuum pulses do not reach within this time out the predetermined value (ex: −0,80 bar), the maximum negative pressure is registered and the cycle goes on.

At the end of the three pulses, the microprocessor calculates the theoretical complementary vacuum and defines the value of the 4th additional pulse with the registered values so that the theoretical air residual percentage can be reached.

Even after the expulsion of the air by the fractionate vacuum, during the build-up of the pressure and sterilisation phases, the condensation has to be regularly drained from the chamber 13. In order to achieve this, both three way valves 10 and 17 are switched in a position which, as explained before, separates the chamber 13 completely from the steam generator 5 and leads the condensation to the condensation collector 11.

The additional advantages of this part of the invention are that the chamber 13 and especially its content, the load, remains even during the pressure pulse as dry as possible, which brings a reduction of the condensation passing through the condenser 19 and the vacuum pump 20 during the vacuum phase. All such condensation heats them up and reduces needlessly their efficiency, so any reduction of condensation passing through the condenser and the vacuum pump is a valuable progress.

Further, the dry state of the chamber 13 and its load improves the drying process and reduces its duration.

So, the invention allows for a perfect obeyance of the well known imperative: "To get a perfect drying, avoid to moisten the load."

During the drying phase, the internal temperature of the steam generator 5 shall be reduced to about 105° C. which allows for a direct draining by opening the waste valve 21 leading to the waste tank 31 without cooling the steam.

Additionally to the described components and pipes appropriate in the described preferred embodiment of the invention, the drawing still discloses other features, elements and parts:

The chamber 13 is provided with two temperature sensors 6' and 6" in order to obtain, at each phase of the process-cycle, with sufficient reliability the temperature prevailing in the chamber. For checking and surveillance purposes, connections 22 for a pressure test and 23 for a temperature test can be used. The chamber 13, having a thermal insulation, is heated by an external heating element 12, its temperature is controlled by an external sensor 24 completely independent of the internal ones.

In order to introduce external sterile air, the chamber 13 is connected to an air inlet by a tube 25, through a valve 28, a one way valve 27 and a bacteriological filter 26. It is necessary, at the end of the sterilisation process, to equilibrate the chamber to the atmospheric pressure prior to the opening of the door.

To the empty the two tanks 1 and 31, drain cocks are foreseen respectively 29 for the pure water, and 29' for the waste. Additionally, a connection to an external pure water tank is provided in a way to have an automatic refilling of the pure water tank 1 by a water pump 30. Both tanks 1 and 31 are most completely watertight and need external connections 32 and 32'.

The tanks are equipped with water level sensors 33, 33' and 33", in order to prevent under-or overfilling. The condenser 19 is air cooled but a water cooled condenser can be used without altering the generic concept of the invention or leaving its scope. The represented membrane pump 20 can be replaced by any other pump used for such applications In the drawing, the pipes are shown in a purely schematic manner, it is clear for the man skilled in the art that various details, which are not part of the invention have to be taken into account. The position of the parts relative to each other, the necessity to use further pumps or different heights of the parts in order to provoke a natural circulation and all mechanical features have no room on a fluid diagram which the drawing is.

Similarly, all kind of materials and the electronic control means have not been discussed, because it is clear for the man skilled in the art that the materials and the electronics usually used in connection with autoclaves can be used for the invention too. Naturally, it is preferred to have a full-automatic autoclave which only has to be loaded and unloaded and detects all kind of failures by itself, stops its functioning and gives the pertinent messages, but it is clear that a "manual handling" is possible too.

Figure 2:
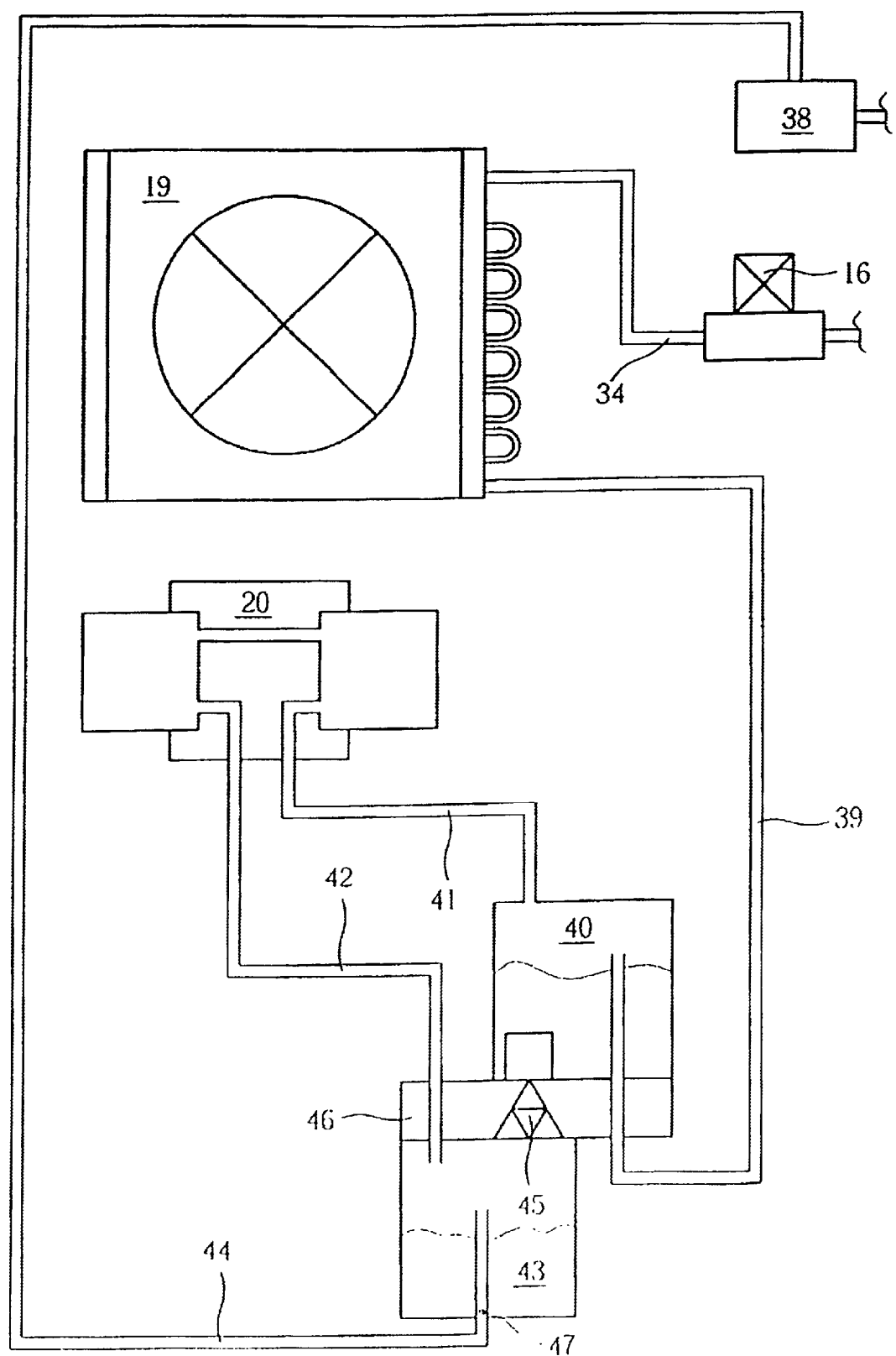
FIG. 2 shows a diagrammatic view of the section of an autoclave according to the invention.

As shown by FIG. 2, the condensate may not just be passed into a waste water tank 31 as in the prior art, but now it is possible, with a clearly reduced power of the vacuum pump 20, to pass the condensate into a combined tank 38 from which it is available again.

This is achieved by the following design: A condensate pipe 39 leads from the condenser 19 to the upper area of a precipitation vessel 40. A vacuum pipe 41 leads from the head of the precipitation vessel 40 to the suction pipe of the vacuum pump 20. A pressure pipe 42 leads from the outlet of the vacuum pump to the upper area of a collector vessel 43, and a transfer pipe 44 leads from the bottom area of said collector vessel to the combined tank 38.

Between the precipitation vessel 40 and the collector vessel 43 there is a connection in which a one-way valve 45 is provided which permits fluid passing only in the direction from the precipitation vessel 40 to the collector vessel 43. In the shown preferred embodiment the precipitation vessel 40 and the collector vessel 43 have identical design and each has the shape of a pot. With the open side the two vessels are mounted on either side of a mounting plate 46, the separator vessel 40 being mounted on its upper side and the collector vessel 43 on its lower side. Thus the connection between the two vessels becomes a bore hole in the mounting plate 46 in which also the check valve or flap trap 45 is positioned. The vessels 40, 43 may either be screwed onto the mounting plate or connected with it by a flange and mounting screws with an intermediate seal.

The fittings for fixing the condensate pipe 39 and the pressure pipe 42 are appropriately provided in the mounting plate so that the vessels 40, 43 need only one mounting point each either on the bottom (or on the top when mounted upside down).

FIGS. 3 to 6 show the sequence of flow of the condensate in the course of a cycle of operation of the autoclave. FIG. 3 shows the precipitation and collector unit according to the invention in the empty state, the condensate pipe 39 extends into the upper area of the precipitation vessel 40, with the vacuum pipe 41 extending from the top surface of that vessel. The precipitation vessel 40 is mounted on the mounting plate 46 where the fixture for the condensate pipe 39 is positioned. Moreover, the connection between the two vessels 40, 43—with a diagrammatic view of a check valve 45 inserted in the drawing is positioned in the mounting plate 46. Somewhat staggered from the precipitation vessel 40 the collector vessel 43 is positioned, with a transfer pipe 44 leading to the tank 38 from its lowest point. The pipe 44 extends preferably up to the upper area of the collector vessel 43, but also has an opening 47 through which the liquid may be discharged at its lower end.

When by opening the valve 16 (FIG. 1 and FIG. 2) the access of steam and condensate to the condenser 19 is permitted and the vacuum pump 20 is put into operation, the condensate (water-steam mixture) gets into the precipitation vessel 40 where the liquid components collect on the bottom and slowly start to fill the vessel 40, while the gaseous components are drawn off through the vacuum pipe 41 to the vacuum pump 20. At the same time pressure is exerted from the outlet of the vacuum pump 20 through the pressure pipe 42 on the collector vessel 43 which forces, as shown diagrammatically, the flap valve 45 into its closed position although the liquid collecting in the precipitation vessel 40 presses on it. The gas flowing through the pressure pipe 42 leaves the collector vessel 43 through the transfer pipe 44 and is discharged in the upper area of the tank 38 (FIG. 2).

FIG. 3 shows the situation arising when the autoclave chamber 13 has been completely emptied (FIG. 1) and the valve 16 (FIG. 2) is closed and the vacuum pump 20 out of operation: in this state the pressure between the (Suction) inlet 41 and the (pressure) outlet 42 of the vacuum pump 20 is equalised which results in a pressure equalisation between the separator vessel 40 and the collector vessel 43, and the weight of the water pressing on the flap valve 45 forces the valve in the open position so that the water flows from the separator vessel 40 into the collector vessel 43 and may also flow into the transfer pipe 44 in so far as said transfer pipe forms a U-shaped sack.

FIG. 4 shows the situation in which the liquid is to be passed from the collector vessel 43 into the tank 38 (FIG. 2). This may be done either in a separate step of the cycle or at the beginning of the next condensation step: the valve 16 is aired (or the condensate pipe 39 after the valve 16 if a separate step is provided), then the vacuum pump 20 is put into operation so that low pressure forms again in the separator vessel 40, while high pressure forms in the collector vessel 43. This results in the closing of the flap valve 45 and passing of this liquid through the transfer pipe 44 into the tank 38 due to the pressure exerted on the liquid in the collector vessel 43; when all the liquid is passed through, gas alone flows through the collector vessel 43 and the transfer pipe 44.

By these inventive features the condensate may not just be pumped, as in the prior art, with a small and compact vacuum pump 20 into a tank at the lowest point of the apparatus from where it has to be passed manually or with a separate pump into the storage tank 1 at the highest point of the apparatus, but it has become possible to perform that transport of the condensate automatically and at an expenditure which is extremely low compared to the result achieved.

The invention may come in different variations, e.g. the two vessels may be of a substantially cylindrical design with an intermediate bottom in which a flap valve is positioned, however, with the condensate pipe 39 and the pressure pipe 42 ending at the surface of the jacket. It is of course also possible to design the two vessels discretely, i.e. not on a common carrying device, but this is not preferred because of the increased demand for fittings, holding devices and space and will be useful only in special cases of application. Of course it is possible to fix the vacuum pump 20 in an appropriate manner dependent on its design also on the mounting plate 46 and dispense with pipes 41 and/or 42 or use pipes of a particularly simple design.

All materials which are used in the prior art for condensers and vessels in autoclaves may be used here, in particular special steel (austenitic stainless steel) or various plastic materials increasingly used in medical apparatus.

What is claimed is:

1. An autoclave for sterilizing medical and in particular dental appliances and instruments, with a chamber (13), in which the appliances to be sterilized are located, with a steam generator (5), connected with the chamber (13) and a condensate pipe (34) connecting the chamber (13) with a condenser (19), and a further pipe (39) connecting the condenser (19) with a separator vessel (40), wherein the condensate (water-steam mixture) in the pipe (39) is passed into said separator vessel (40), a connecting pipe (41) extends from an upper area of said separator vessel (40), preferably from its highest point, to a vacuum pump (20), said separator vessel (40) is provided in its lower area, preferably at its lowest point, with a one-way valve (45) which in the presence of a predetermined pressure difference permits discharge of fluid from the separator vessel (40) into a collector vessel (43), a pressure pipe (42) coming from the vacuum pump (20) ends in an upper area of said collector vessel (43) and a transfer pipe (44) leads into a main tank (38) of the autoclave from a lower area of said collector vessel (43).

2. An autoclave according to claim 1, wherein said separator vessel (40) and said collector vessel (43) have pot-like shape and are identical, and said separator vessel (40) and said collector vessel (43) are mounted on a mounting plate (46) in a staggered way, and the one-way valve (45) is positioned in the mounting plate (45).

* * * * *